United States Patent [19]
Beregi et al.

[11] 3,956,501
[45] May 11, 1976

[54] N-SUBSTITUTED GLYCINATES

[75] Inventors: Laszlo Beregi, Boulogne; Charles Malen, Fresnes; Pierre Hugon, Rueil Malmaison; Jacques Duhault, Chatou, all of France

[73] Assignee: Science Union et Cie, Societe Francaise de Recherche Medical, France

[22] Filed: Aug. 5, 1974

[21] Appl. No.: 494,748

[30] Foreign Application Priority Data
Aug. 16, 1973 United Kingdom............... 38730/73

[52] U.S. Cl............................ 424/282; 260/340.5; 260/471 A; 424/309
[51] Int. Cl.².............. C07C 101/16; C07D 317/64
[58] Field of Search..................... 260/340.5, 471 A; 424/282, 309

[56] References Cited
UNITED STATES PATENTS
3,856,857   12/1974   Beregi et al.................260/471 A Primary Examiner—Richard L. Raymond
Attorney, Agent, or Firm—Gordon W. Hueschen

[57] ABSTRACT

N-substituted glycinates of the formula:

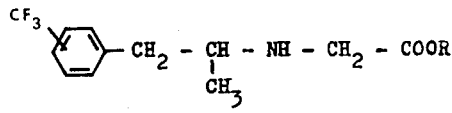

optical isomers and acid addition salts thereof, wherein R is cyclopentyl, cyclohexyl, benzyl, halobenzyl, lower alkylbenzyl, lower alkoxybenzyl, methylenedioxybenzyl or trifluoromethylbenzyl.

These compounds are used as medicines especially in the treatment of obesity or other metabolic diseases needing weight reduction and regulation.

9 Claims, No Drawings

N-SUBSTITUTED GLYCINATES

The present invention provides N-substituted glycinates and their optical isomers of the general formula I:

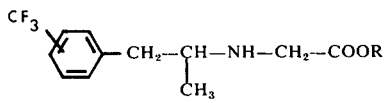

wherein R is selected from the group consisting of cyclopentyl, cyclohexyl and benzyl radicals and benzyl radicals substituted by one or more substituents selected from the group consisting of halogen atoms, alkyl and alkoxy radicals each having from 1 to 4 carbon atoms inclusive, methylenedioxy and trifluoromethyl radicals; and acid addition salts, especially physiologically tolerable acid addition salts thereof.

Though the trifluoromethyl radical might be bounded in any position on the benzene nucleus, the preferred compounds are those wherein it is bounded in meta-position.

The French Pat. No. 2,034,571 entitled "Amino Acids and their derivatives" discloses, among others, esters of aliphatic alcohols from 1 to 4 carbon atoms inclusive. We have now surprisingly found that the glycinates of the general formula I have a much lower toxicity, while the anorexigenic activity studied in the rat and in the dog is generally higher than that observed with the above mentioned compounds.

The compounds of the general formula I are new and are prepared by reacting a trifluoromethylphenyl isopropylamine of the formula II:

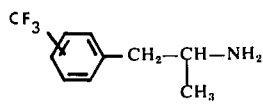

with a chloroacetate of the general formula III:

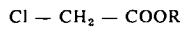

wherein R has the meanings given above.

This reaction is advantageously performed by refluxing in a suitable organic solvent such for example as benzene.

All compounds of general formula I possess an asymmetric carbon atom and exist in form of optically active isomers. These optical isomers may be prepared from the corresponding d or l - phenyl isopropylamines.

The compounds of the general formula I and their optical isomers may be converted into addition salts with mineral or organic acids such as, for example, hydrochloric, hydrobromic, sulfuric, phosphoric, sulfamic, acetic, propionic, maleic, fumaric, tartaric, citric, oxalic, methanesulfonic, benzoic and anthranilic acids.

The compounds of the general formula I, optical isomers and physiologically tolerable addition salts thereof, possess valuable pharmacological and therapeutic properties, particularly appetite inhibiting and lipid and carbohydrate metabolism regulating properties. They so can be used as medicines especially in the treatment of obesity or other metabolic diseases needing weight reduction and regulation.

Their toxicity is low and their $LD_{50}$ determined in mice varies from 400 to >1600 mg/kg per orally.

Their anorexigenic activity was studied in rats and dogs. It was observed that the food intake of rats was reduced by 18 to 85 percent, 2 hours after administering the products at the dose of 1 to 10 mg/kg P.O. The food intake of dogs was reduced by 10 to 100 percent with the dose of 5 to 10 mg/kg in the same conditions.

The present invention also provides pharmaceutical compositions which contains a compound of the general formula I, an optical isomer or a physiologically tolerable salt thereof in admixture or conjunction with a pharmaceutically suitable carrier, such for example, as distilled water, glucose, lactose, starch, talc, magnesium stearate, ethyl cellulose or cocoa butter.

The so-obtained pharmaceutical compositions are advantageously in unit dosage form and may contain from 5 to 200 mg of the active ingredient.

These pharmaceutical compositions may be in form of tablets, dragees, capsules, suppositories or injectable or drinkable solutions and may be administered by oral, rectal or parenteral route at a dose of 5 to 200 mg, 1 to 5 times a day.

The following Examples illustrate the invention, the parts being by weight and the melting points being determined on a Kofler block.

EXAMPLE 1

Benzyl N-[1-(3-trifluoromethylphenyl) prop-2-yl] glycinate

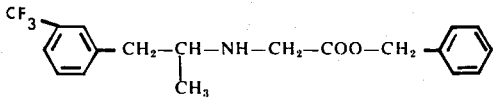

92.3 parts of benzyl chloroacetate were added to a solution of 203 parts of 1-(3-trifluoromethylphenyl)-2-aminopropane in 400 parts of anhydrous benzene. The mixture was refluxed for 4 hours. After being allowed to cool at room temperature, the salt was filtered off. The distillation of the residual liquid yielded 92 parts of benzyl N-[1-(3-trifluoromethylphenyl) prop-2-yl] glycinate, B.P./0.4 mm Hg: 185°–190°C. The corresponding hydrochloride, recrystallized in isopropanol, melted at 170°–172°C.

EXAMPLES 2–14

The following compounds were prepared according to the method described in Example 1, from 1-(3-trifluoromethylphenyl)-2-aminopropane:

2. Para-methylbenzyl N-[1-(3-trifluoromethylphenyl) prop-2-yl] glycinate, B.P./0.4 mm Hg: 160°–165°C, M.P. of its hydrochloride: 160°–162°C (isopropanol), starting from para-methylbenzyl chloroacetate.

3. Cyclopentyl N-[1-(3-trifluoromethylphenyl) prop-2-yl] glycinate, B.P./0.15 mm Hg: 135°-139°C, M.P. of its hydrochloride: 168°-169°C (isopropanol, starting from cyclopentyl chloroacetate.

4. Cyclohexyl N-[1-(3-trifluoromethylphenyl) prop-2-yl] glycinate, B.P./0.1 mm Hg: 140°-147°C, M.P. of its hydrochloride: 207°-208°C (isopropanol), starting from cyclohexyl chloroacetate.

5. Para-fluorobenzyl N-[1-(3-trifluoromethylphenyl) prop-2-yl] glycinate, M.P. of its hydrochloride: 152°C (isopropanol), starting from para-fluorobenzyl chloroacetate.

6. Para-chlorobenzyl N-[1-(3-trifluoromethylphenyl) prop-2-yl] glycinate, B.P./0.1 mm Hg: 160°-165°C, M.P. of its hydrochloride: 139°-140°C (ethyl acetate), starting from para-chlorobenzyl chloroacetate.

7. Meta-trifluoromethylbenzyl N-[1-(3-trifluoromethylphenyl) prop-2-yl] glycinate, M.P. of its hydrochloride: 148°C (ethyl acetate), starting from meta-trifluoromethylbenzyl chloroacetate.

8. 3,4-methylenedioxybenzyl N-[1-(3-trifluoromethylphenyl) prop-2-yl] glycinate, M.P. of its hydrochloride: 142°C (ethyl acetate), starting from 3,4-methylenedioxybenzyl chloroacetate.

9. d-benzyl N-[1-(3-trifluoromethylphenyl) prop-2-yl] glycinate, B.P./0.2 mm Hg: 145°-148°C; for its hydrochloride: M.P. 190°-191°C (ethanol), $[\alpha]_D^{26} = + 10.7° \pm 1°$ (C.6, methanol), starting from benzyl chloroacetate and d-1-(3-trifluoromethylphenyl)-2-aminopropane.

10. l-benzyl N-[1-(3-trifluoromethylphenyl) prop-2-yl] glycinate, B.P./0.3 mm Hg: 152°-163°C; for its hydrochloride: M.P. 188°-189°C (ethanol), $[\alpha]_D^{29} = -10.6° \pm 1°$ (C.8, methanol), starting from benzyl chloroacetate and l-1-(3-trifluoromethylphenyl)-2-aminopropane.

11. d-cyclopentyl N-[1-(3-trifluoromethylphenyl) prop-2-yl] glycinate, B.P./0.4 mm Hg: 132°-134°C; for its hydrochloride: M.P. 200°C (isopropanol), $[\alpha]_D^{25} = + 10.6°$ (C.8, methanol), starting from cyclopentyl chloroacetate and d-1-(3-trifluoromethylphenyl)-2-aminopropane.

12. Ortho-methylbenzyl N-[1-(3-trifluoromethylphenyl) prop-2-yl] glycinate, starting from ortho-methylbenzyl chloroacetate.

13. Meta-methylbenzyl N-[1-(3-trifluoromethylphenyl) prop-2-yl] glycinate, starting from meta-methylbenzyl chloroacetate.

14. Para-methoxybenzyl N-[1-(3-trifluoromethylphenyl) prop-2-yl] glycinate, starting from para-methoxybenzyl chloroacetate.

According to the method used in Examples 1 to 14 but using 1-(2-trifluoromethylphenyl)-2-aminopropane, and 1-(4-trifluoromethylphenyl)-2-aminopropane, instead of 1-(3-trifluoromethylphenyl)-2-aminopropane, there were obtained the corresponding N-[1-(2-trifluoromethylphenyl) prop-2-yl] glycinates and N-[1-(4-trifluoromethylphenyl) prop-2-yl] glycinates.

We claim:
1. A compound selected from the group consisting of:

A. N-substituted glycinates of the general formula:

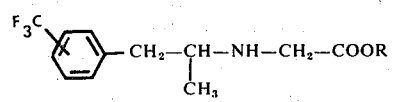

wherein:
R is selected from the group consisting of cyclopentyl, cyclohexyl, benzyl, chlorobenzyl, fluorobenzyl, alkylbenzyl and alkoxybenzyl wherein the alkyl and alkoxy moieties have from 1 to 4 carbon atoms inclusive, methylenedioxybenzyl and trifluoromethylbenzyl, B. their optical isomers and
C. physiologically tolerable acid addition salts thereof.

2. Compounds of claim 1 which are N-[1-(3-trifluoromethylphenyl) prop-2-yl] glycinates, their optical isomers and their physiologically tolerable acid addition salts.

3. A compound of claim 1 which is benzyl N-[1-(3-trifluoromethylphenyl) prop-2-yl] glycinate.

4. A compound of claim 1 which is d-benzyl N-[1-(3-trifluoromethylphenyl) prop-2-yl] glycinate.

5. A compound of claim 1 which is cyclopentyl N-[1-(3-trifluoromethylphenyl) prop-2-yl] glycinate.

6. A compound of claim 1 which is d-cyclopentyl N-[1-(3-trifluoromethylphenyl) prop-2-yl] glycinate.

7. A compound of claim 1 which is cyclohexyl N-[1-(3-trifluoromethylphenyl) prop-2-yl] glycinate.

8. A pharmaceutical composition containing as active principle at least one compound of claim 1 in an amount of 5 to 200 mg together with a suitable pharmaceutical carrier.

9. A method of treating a living animal body afflicted with obesity or metabolic disease requiring weight reduction or regulation comprising the step of administering an amount of a compound of claim 1 which is effective for the alleviation of the said condition.

* * * * *